United States Patent [19]
Herbstman

[11] 4,409,417
[45] Oct. 11, 1983

[54] PROCESS OF DEHYDROGENATION OF HYDROCARBONS

[75] Inventor: Sheldon Herbstman, Spring Valley, N.Y.

[73] Assignee: Texaco Inc., White Plains, N.Y.

[21] Appl. No.: 401,477

[22] Filed: Jul. 26, 1982

[51] Int. Cl.$^3$ .............................................. C07C 5/36
[52] U.S. Cl. .................................. 585/660; 585/654; 208/138
[58] Field of Search ........................ 585/654, 660, 661

[56] References Cited

U.S. PATENT DOCUMENTS

| | | | |
|---|---|---|---|
| 3,644,200 | 2/1972 | Young | 208/120 |
| 3,723,557 | 3/1973 | Hayes | 585/660 |
| 3,742,078 | 6/1973 | Hayes | 585/660 |
| 3,903,191 | 9/1975 | Pollitzer | 585/660 |
| 3,907,921 | 9/1975 | Winter | 585/660 |
| 3,917,540 | 11/1975 | Pollitzer | 585/660 |
| 4,000,210 | 12/1976 | Sensel et al. | 585/660 |
| 4,177,218 | 12/1979 | Antos | 585/660 |
| 4,313,020 | 1/1982 | Antos | 585/660 |

Primary Examiner—Delbert E. Gantz
Assistant Examiner—A. Pal
Attorney, Agent, or Firm—Robert A. Kulason; Robert Knox; Carl G. Seutter

[57] ABSTRACT

Isobutane may be dehydrogenated to isobutylene with increased selectivity by passing isobutane together with hydrogen and ammonia at 700° F.–1200° F. in the presence of a supported catalyst containing Group IA metals (Li, K) plus Pt-Re, Pt-Ge, or Pt-Re-Ge.

16 Claims, No Drawings

PROCESS OF DEHYDROGENATION OF HYDROCARBONS

FIELD OF THE INVENTION

This invention relates to dehydrogenation of hydrocarbons. More particularly it relates to conversion of isobutane to isobutylene in high selectivity.

BACKGROUND OF THE INVENTION

As is well known to those skilled in the art, it is desired to convert hydrocarbons such as alkanes to unsaturated hydrocarbons in order to permit utilization of the latter in any of a wide variety of processes.

It is an object of this invention to provide a process for dehydrogenating a dehydrogenatable hydrocarbon under conditions of improved selectivity. Other objects will be apparent to those skilled in the art.

STATEMENT OF THE INVENTION

In accordance with certain of its aspects, the method of this invention for dehydrogenating a dehydrogenatable hydrocarbon comprises passing, at dehydrogenating conditions, into contact with a supported dehydrogenation catalyst containing (i) a noble Group VIII metal, (ii) a metal of Group VII B or Group IV A and (iii) a metal of Group IA, a charge composition containing dehydrogenatable hydrocarbon, hydrogen, and ammonia thereby forming a product dehydrogenated gas stream; and recovering said product dehydrogenated gas stream.

DESCRIPTION OF THE INVENTION

The charge dehydrogenatable hydrocarbons which may be dehydrogenated by the process of this invention may typically include those having two to 30 carbon atoms per molecule and containing at least one pair of adjacent carbon atoms having hydrogen attached thereto i.e., organic compounds capable of being hydrogenated to produce products containing the same number of carbon atoms but fewer hydrogen atoms, and capable of being vaporized at the dehydrogenation conditions used herein. Suitable dehydrogenatable hydrocarbons include: aliphatic compounds containing two to 30 carbon atoms per molecule, alkyl-aromatic hydrocarbons where the alkyl group contains two to six carbon atoms, and naphthenes or alkyl-substituted naphthenes. Specific examples of suitable dehydrogenatable hydrocarbons are: (1) alkanes such as ethane, propane, n-butane, isobutane, n-pentane, isopentane, neopentane, n-hexane, 2-methylpentane, 2,2-dimethylbutane, n-heptane, 2-methylhexane, 2,2,3-trimethylbutane, etc.; (2) naphthenes such as cyclopentane, methylcyclopentane, ethylcyclopentane, n-propylcyclopentane, cyclohexane, isopropylcyclopentane, 1,3-dimethylcyclohexane, etc. and, (3) alkylaromatics such as ethylbenzene, n-propylbenzene, n-butylbenzene, 1,3,5-triethylbenzene, isopropylbenzene, isobutylbenzene, ethylnaphthalene, etc.

In a preferred embodiment, the dehydrogenatable hydrocarbon is a normal paraffin hydrocarbon having about four to about 30 carbon atoms per molecule. For example, normal paraffin hydrocarbons containing about 10 to 15 carbon atoms per molecule are dehydrogenated by the subject method to produce the corresponding normal mono-olefin; n-alkanes having 12 to 18 carbon atoms per molecule can be dehydrogenated to the corresponding normal mono-olefin. Similarly, n-alkanes having six to 10 carbon atoms per molecule can be dehydrogenated to form the corresponding mono-olefins which can be hydrated to produce valuable alcohols. Preferred feed streams for the manufacture of detergent intermediates contain a mixture of four or five adjacent normal paraffin homologues such as $C_{10}$ to $C_{18}$, $C_{11}$ to $C_{14}$, $C_{11}$ to $C_{18}$ etc.

In practice of the process of this invention, dehydrogenation may be carried out in the presence of supported dehydrogenation catalyst containing (i) a noble Group VIII metal, (ii) a metal of a Group VII B or Group IV A and (iii) a metal of Group IA.

The noble Group VIII metals which may be present may include platinum, Pt; iridium, Ir; osmium Os; palladium, Pd; rhodium, Rh; or ruthenium, Ru. The preferred metal is platinum. This component is preferably present in the catalyst composition in amount of 0.01–2 w%, preferably 0.05–1 w%, say about 0.5 w% of the catalyst composition.

The Group VII B metal which may be present may include manganese, Mn or more preferably rhenium, Re, in amount of 0–2 w%, preferably 0.05–1 w%, say about 0.5 w% of catalyst composition.

The Group IV A metal which may be present may include tin, Sn, lead, Pb, or more preferably germanium, Ge in amount of 0–2 w%, preferably 0.05–1 w%, say about 0.5 w% of catalyst composition.

The metal of Group IA may include lithium, Li; sodium, Na; potassium, K; ruthidium, Rb; or caesium, Cs. Preferred is potassium. This component may be present in amount of 0.01–2 w% of catalyst composition.

The support may be a porous carrier material of high surface area typified by activated carbon, silica, alumina, silica-alumina, clays, refractory oxides, crystalline aluminosilicates including zeolites, etc. Preferred support may be gamma alumina in the form of cylinders or spheres of average diameter of 1–3 mm.

Catalyst may be prepared by impregnating the support with the metals. Preferably the support may be immersed in one or more solutions of soluble salts of the metals and dried and calcined between immersions. Catalyst preparation may preferably be as carried out in a manner generally similar to that disclosed in U.S. Pat. No. 3,649,564 or in U.S. Pat. No. 3,723,557.

One preferred catalytic composite (Pt-Re-alkali metal) comprises a combination of a platinum component, a rhenium component, and an alkali metal component with an alumina carrier material in amounts sufficient to result in the composite containing from about 0.05 to about 1 wt. % platinum, about 0.05 to about 1 wt. % rhenium, and about 0.25 to about 3.5 wt. % of the alkali metal. Another preferred composite may contain Pt-Ge-K-$Al_2O_3$.

Preferred catalytic composites include the following:
(1) a catalytic composite comprising 0.375 wt. % platinum, 0.2 wt. % rhenium, and 0.5 wt. % lithium combined with an alumina carrier material.
(2) a catalytic composite comprising 0.375 wt. % platinum, 0.5 wt. % germanium, and 0.5 wt. % potassium combined with an alumina carrier material; and
(3) a catalytic composite comprising 0.375 wt. % platinum, 0.375 wt. % rhenium, 0.375 wt. % germanium, and 0.5 wt. % lithium combined with an alumina carrier material.

The resulting composite generally will be dried at a temperature of about 200° F. to about 600° F. for a period of from about 2 to 24 hours or more, and finally calcined at a temperature of about 600° F. to about 1,100° F. in an air atmosphere for a period of about 0.5 to 10 hours, preferably about 1 to about 5 hours in order to substantially convert the metallic components to the oxide form. When acidic components are present in any of the reagents used to effect incorporation of any one of the components of the subject composite, it is good practice to subject the resulting composite to a high temperature treatment with steam or with a mixture of steam and air, either after or before the calcination step described above, in order to remove as much as possible of the undesired acidic component. For example, when the platinum group component is incorporated by impregnating the carrier material with chloroplatinic acid, it is preferred to subject the resulting composite to a high temperature treatment with steam in order to remove as much as possible of the undesired chloride.

It is preferred that the resultant calcined catalytic composite be subjected to a substantially water-free reduction prior to its use in the conversion of hydrocarbons. This step is designed to insure a uniform and finely divided dispersion of the metallic components throughout the carrier material. Preferably, substantially pure and dry hydrogen (i.e., less than 20 vol. ppm water) is used as the reducing agent in this step. The reducing agent is contacted with the calcined composite at a temperature of about 500° F. to about 1,200° F., a gas hourly space velocity of about 100 to about 5,000 hr.$^{-1}$, and for a period of time of about 0.5 to 10 hours or more, effective to substantially reduce at least the platinum group component. This reduction treatment may be performed in situ as part of a start-up sequence if precautions are taken to predry the plant to a substantially water-free state and if substantially water-free hydrogen is used.

The resulting reduced catalytic composite may, in some cases, be beneficially subjected to a pre-sulfiding operation designed to incorporate in the catalytic composite from about 0.05 to about 0.50 wt. % sulfur calculated on an elemental basis. Preferably, this pre-sulfiding treatment takes place in the presence of hydrogen and a suitable sulfur-containing compound such as hydrogen sulfide, lower molecular weight mercaptans, organic sulfides, etc. Typically, this procedure comprises treating the reduced catalyst with a sulfiding gas such as a mixture containing a mole ratio of $H_2$ to $H_2S$ of about 10:1 at conditions sufficient to effect the desired incorporation of sulfur, generally including a temperature ranging from about 50° F. up to about 1,100° F. or more. This pre-sulfiding step can be performed in situ or ex situ.

According to the method of the present invention, the dehydrogenatable hydrocarbon is contacted with a catalytic composite of the type described above in a dehydrogenation zone at dehydrogenation conditions. This contacting may be accomplished by using the catalyst in a fixed bed system, a moving bed system, a fluidized bed system, or in a batch type operation; however, it is preferred to use a fixed bed system. In this system, the hydrocarbon feed stream is preheated to the desired reaction temperature and then passed into a dehydrogenation zone containing a fixed bed of the catalyst. The dehydrogenation zone may be in one or more separate reactors with suitable heating means therebetween to insure that the desired conversion temperature is maintained at the entrance to each reactor. The reactants may be contacted with the catalyst bed in either upward, downward, or radial flow fashion, with the latter being preferred. The reactants may be in the liquid phase, a mixed liquid-vapor phase, or a vapor phase when they contact the catalyst, with best results obtained in the vapor phase.

Although hydrogen is the preferred diluent for use in the subject dehydrogenation method, in some cases other art-recognized diluents may be advantageously utilized such as steam, methane, carbon dioxide, and the like diluents. Hydrogen is preferred because it serves the dual-function of not only lowering the partial pressure of the dehydrogenatable hydrocarbon, but also of suppressing the formation of hydrogen-deficient, carbonaceous deposits on the catalytic composite. Ordinarily, hydrogen is utilized in amounts sufficient to insure a hydrogen to hydrocarbon mole ratio of about 1:1 to about 20:1, with best results obtained in the range of about 1.5:1 to about 10:1. The hydrogen stream charged to the dehydrogenation zone will typically be recycle hydrogen obtained from the effluent stream from this zone after a suitable separation step.

It is a particular feature of the process of this invention that catalyst selectivity may be enhanced by carrying out dehydrogenation in the presence of ammonia. Preferably ammonia may be admitted with hydrogen and charge hydrocarbon. The ammonia may be present in amount to provide a mole ratio of ammonia to hydrocarbon of 0.05–0.5, preferably 0.1–0.3, say about 0.15:1.

In accordance with the practice of this process of this invention, the reaction may be carried out at the following conditions:

TABLE

| Condition | Broad | Preferred | Typical |
|---|---|---|---|
| Temperature °F. | 700–1400 | 900–1200 | 1050 |
| Pressure atm | 0.1–10 | 0.5–3 | 1 |
| Hydrocarbon LHSV | 1–40 | 25–35 | 30 |
| Mole Ratio $H_2$:HC | 1–20 | 1.5–10 | 5 |
| $NH_3$:HC | 0.05–0.5:1 | 0.1–0.3:1 | 0.15:1 |

Effluent from dehydrogenation may contain unconverted dehydrogenatable hydrocarbons, hydrogen, ammonia, and products of the dehydrogenation reaction. This stream is typically cooled and passed to a separating zone wherein a hydrogen-rich vapor phase is allowed to separate from a hydrocarbon-rich liquid phase. In general, it is usually desired to separate the unreacted dehydrogenatable hydrocarbon from this hydrocarbon-rich liquid phase and this can be accomplished in any suitable manner known to the art such as by fractional distillation or by passing the hydrocarbon-rich liquid phase through a bed of suitable adsorbent material which has the capability to selectively retain the dehydrogenated hydrocarbons contained therein or by contacting same with a solvent having a high selectivity for the dehydrogenated hydrocarbons.

In the case where the dehydrogenated hydrocarbon is a mono-olefin, suitable adsorbents having this capability are activated silica gel, activated carbon, activated alumina, various types of specially prepared molecular sieves, and the like adsorbents. In another typical case, the dehydrogenated hydrocarbons can be separated from the unconverted dehydrogenatable hydrocarbons by utilizing the inherent capability of the dehydrogenated hydrocarbons to enter into several well known chemical reactions such as alkylation, ether formation, oligomerization, halogenation, sulfonation, hydration, oxidation, and the like reactions. Irrespective of how the dehydrogenated hydrocarbons are separated from the unreacted hydrocarbons, a stream containing the unreacted dehydrogenatable hydrocarbons will typically be recovered from this hydrocarbon separation step and recycled to the dehydrogenation step. Likewise, the gas phase present in the gas separating zone will be withdrawn therefrom, a portion of it vented from the system in order to remove the net hydrogen make, and the remaining portion is typically recycled, through suitable compressing means, to the dehydrogenation step in order to provide diluent hydrogen and ammonia therefor.

It is a feature of the process of this invention that it is possible to effect dehydrogenation of hydrocarbons in a manner to achieve increased selectivity and initial yield.

DESCRIPTION OF PREFERRED EMBODIMENTS

Practice of the process of this invention will be apparent to those skilled in the art from the following wherein, as elsewhere in this specification, all parts are parts by weight unless otherwise specified.

EXAMPLE I*

In Examples I-VII, the catalyst employed was prepared from UOP R-16 H brand of catalyst which contained 0.375 w% platinum, 0.2 w% rhenium on gamma alumina (prepared generally as disclosed in U.S. Pat. No. 3,723,557) to which has been added 0.5 w% potassium by immersing the catalyst in aqueous potassium carbonate for one hour. Potassium carbonate is presented in the aqueous solution in amount calculated to yield 0.5 w%. potassium on the catalyst after calcining in air at 1000° F. The solution is removed by evaporation on a steam plate. The catalyst is then dried at 1000° F. and calcined in hydrogen at 550° F. for 2 hours before introduction of alkane feed at required run temperature.

In each of Examples I-VII, isobutane (8 WHSV) and hydrogen (1.0 CFH, cubic feet per hour, corresponding to a mole ratio of hydrogen to hydrocarbon of 0.67:1) was passed over the catalyst at 1060° F. and 25 psig.

For each example there are calculated the isobutylene yield (the weight of isobutylene produced per unit weight of isobutane charged) and the selectivity (the weight of isobutylene produced per unit weight of dehydrogenations products not including isobutane charged).

In control Example I, the isobutane charged was of purity 99.0 w% and contained 200 ppm water.

EXAMPLE II*

In this control Example, the isobutane charge was dried by passage at 100° F. through a bed of molecular sieve to a water content of 10 ppm.

EXAMPLE III*

In this control Example, the catalyst was sulfided by passing hydrogen sulfide (mole ratio of hydrogen sulfide to hydrocarbon of 0.05:1) through the bed with the hydrocarbon charge for 2 hours at 550° F., then shutting off the hydrogen sulfide, starting up the hydrogen feed, and reducing at 550° F. for 4 hours.

EXAMPLE IV*

In this control Example, the hydrogen flow rate was 4.0 CFH, double that of Example I—but all other conditions were as in Example I.

EXAMPLE V*

In this control Example, the conditions of Example I were duplicated except that the pressure was increased to 125 psig.

EXAMPLE VI

In this Example of the process of this invention, the procedure of Example I was followed except that there is also injected into the feed ammonia in amount of 0.2 CFH (corresponding to a mole ratio of ammonia to hydrocarbon feed of 0.145:1).

EXAMPLE VII

In this Example which represents the best mode known to me at this time of practicing the process of this invention, the charge to the reaction is 8 WHSV of isobutane (99.5% pure, containing 10 ppm water), one CFH (cubic feet per hour) of hydrogen corresponding to a hydrogen to hydrocarbon mole ratio of 0.73:1, and 0.4 CFH of ammonia corresponding to ammonia to hydrocarbon mole ratio of 0.13:1. Reaction is carried out at 1060° F./25 psig over the same catalyst as is used in Examples I-IV.

The results may be tabulated as follows:

TABLE

Catalyst: 0.5%K - 0.375% Pt - 0.2% Re - gamma alumina
1060° F. at 25 psig

| Example | Conditions | Isobutylene Yield w %*** | | | Selectivity** |
|---|---|---|---|---|---|
| | | Initial (7 hr) | 25 hr | 31 hr | |
| I | Base | 23.8 | 21.2 | 20.3 | 72.3 |
| II | Dry isobutane* | 21.8 | 19.4 | | 75.6 |
| III | Sulfided Catalyst* Dry Isobutane | 23.8 | 21.5 | 20.5 | 78.2 |
| IV | Increase hydrogen rate to 4.0 CFH | 19.6 | 19.8 | 18.9 | 59.8 |
| V | Increase pressure to 125 psig | 9.0 | 9.4 | — | 39.7 |
| VI | Ammonia injection 0.2 CFH | 25.0 | 21.8 | 21.4 | 80.2 |
| VII | Ammonia injection 0.4 CFH | 27.6 | 21.3 | 20.7 | 84.7 |

*Dry isobutane contains 10 ppm water
**Selectivity is (isobutylene/isobutane consumed ) × 100
***Yield is (isobutylene/isobutane charged) × 100

From the above table, the following conclusions will be apparent:
(i) The initial isobutylene yield of Example VII increased by as much as 26.5% over the yield obtained in Example II;
(ii) Use of lesser amounts of ammonia (Example VI) gives substantial improvement in initial isobutylene yield;
(iii) Use of the process of this invention permits attainment of isobutylene yield at 25 hours which are essentially equivalent to those achieved at 7 hours with Examples I-II;
(iv) The selectivity to desired product isobutylene using the process of this invention may be as much as 18% better (84.7/72.3) then control processes.

EXAMPLE VIII

Results comparable to those obtained in Examples I–VII may be attained by adding 0.5 w% potassium to a catalyst containing 0.375 w% platinum—0.25 w% germanium—gamma alumina (typified by the UOP R-22 brand of catalyst) and dehydrogenation in the presence of ammonia.

EXAMPLE IX 0.5K—0.375 Pt—0.20 Re on gamma alumina

In this example, another catalyst is disclosed. 100 g of 1/16 inch gamma alumina extrudates are impregnated with a 100 gram solution containing 1.1 grams of chloroplatinic acid and 0.4 grams of perrhenic acid in 0.25 N nitric acid and 0.1 N hydrochloric acid solution. The catalyst is dried initially at 225° F. for 4 hours and then calcined in air at 1000° F. for 12 hours. The calcined catalyst is reimpregnated with 1.2 g of potassium carbonate in 60 g of water, dried at 225° F. for 6 hours and recalcined at 1000° F. for 12 hours.

Prior to use the catalyst is reduced for 12 hours at 550° F., 100 psig. in a 3 CFH hydrogen stream (99+%) free of moisture or impurities such as sulfur compounds.

Although this invention has been illustrated by reference to specific embodiments, it will be apparent to those skilled in the art that various changes and modifications may be made which clearly fall within the scope of this invention.

I claim:

1. The method of dehydrogenating a dehydrogenatable hydrocarbon which comprises passing, at dehydrogenating conditions, into contact with a supported dehydrogenation catalyst containing (i) a noble Group VIII metal, (ii) a metal of Group VII B or Group IV A, and (iii) a metal of Group IA, a charge composition containing dehydrogenatable hydrocarbon, hydrogen, and ammonia thereby forming a product dehydrogenated gas stream; and recovering said product dehydrogenated gas stream.

2. The method of dehydrogenating a dehydrogenatable hydrocarbon as claimed in claim 1 wherein ammonia is present during dehydrogenation in amounts of 0.05–0.5 moles per mole of charge dehydrogenatable hydrocarbon.

3. The method of dehydrogenating a dehydrogenatable hydrocarbon as claimed in claim 1 wherein ammonia is present during dehydrogentation in amount of 0.1–0.3 moles per mole of charge dehydrogenatable hydrocarbon.

4. The method of dehydrogenating a dehydrogenatable hydrocarbon as claimed in claim 1 wherein ammonia is present during dehydrogenation in amounts of about 0.15 moles per mole of charge dehydrogenatable hydrocarbon.

5. The method of dehydrogenating a dehydrogenatable hydrocarbon as claimed in claim 1 wherein said noble Group VIII metal is platinum.

6. The method of dehydrogenating a dehydrogenatable hydrocarbon as claimed in claim 1 wherein said catalyst contains rhenium as the metal of Group VII B or Group IV A.

7. The method of dehydrogenating a dehydrogenetable hydrocarbon as claimed in claim 1 wherein said catalyst contains germanium as the metal of Group VII B or Group IV A.

8. The method of dehydrogenating a dehydrogenatable hydrocarbon as claimed in claim 1 wherein said catalyst contains potassium as the metal of Group IA.

9. The method of dehydrogenating a dehydrogenatable hydrocarbon as claimed in claim 1 wherein said catalyst contains lithium as the metal of Group IA.

10. The method of dehydrogenating a dehydrogenatable hydrocarbon as claimed in claim 1 wherein said catalyst contains an inorganic oxide as support.

11. The method of dehydrogenating a dehydrogenatable hydrocarbon as claimed in claim 1 wherein said catalyst contains alumina as support.

12. The method of dehydrogenating a dehydrogenatable hydrocarbon as claimed in claim 1 wherein dehydrogenating conditions include 700° F.–1200° F. at 0.1–10 atmospheres.

13. The method of dehydrogenating a dehydrogenatable hydrocarbon which comprises passing, at 700° F.–1200° F. and 0.1–10 atmospheres, into contact with a supported dehydrogenation catalyst containing platinum, rhenium, and potassium on gamma alumina, a dehydrogenatable hydrocarbon, hydrogen, and ammonia, said ammonia being present in amount of 0.05–0.5 moles per mole of charge dehydrogenatable hydrocarbon, thereby forming a product dehydrogenated gas stream; and recovering said product dehydrogenated gas stream.

14. The method of dehydrogenating a dehydrogenatable hydrocarbon as claimed in claim 13 wherein said catalyst contains about 0.05–1 w% platinum, 0.05–1 w% rhenium, and 0.25–3.5 w% potassium on gamma alumina.

15. The method of dehydrogenating a dehydrogenatable hydrocarbon which comprises passing, at 700° F.–1200° F. and 0.1–10 atmospheres, into contact with a supported dehydrogenation catalyst containing platinum, germanium, and potassium on gamma alumina, a dehydrogenatable hydrocarbon, hydrogen, and ammonia, said ammonia being present in amounts of 0.05–0.5 moles per mole of charge dehydrogenatable hydrocarbon, thereby forming a product dehydrogenated gas stream;

recovering said product dehydrogenated gas stream.

16. The method of dehydrogenating a dehydrogenatable hydrocarbon as claimed in claim 15 wherein said catalyst contains about 0.05–1 w% platinum, 0.05–1 w% germanium and 0.25–3.5 w% potassium on gamma alumina.

* * * * *